United States Patent [19]

Arrigoni et al.

[11] 4,191,047

[45] Mar. 4, 1980

[54] DEVICE FOR DETECTING THE INITIAL SETTLING OF THE SOLID PHASE IN SOLID-LIQUID SUSPENSIONS

[75] Inventors: Virgilio Arrigoni, San Donato, Milan; Dario Ercolani, Urbino; Francesco Ferrini, Fano, all of Italy

[73] Assignee: Snamprogetti, S.p.A., San Donato Milan; Italy

[21] Appl. No.: 900,738

[22] Filed: Apr. 27, 1978

[30] Foreign Application Priority Data

May 5, 1977 [IT] Italy ................. 23192 A/77

[51] Int. Cl.² ........................................... G01N 33/00
[52] U.S. Cl. ...................................................... 73/61.4
[58] Field of Search ................ 73/61.4, 194 E, 194 F

[56] References Cited

U.S. PATENT DOCUMENTS

| | | | |
|---|---|---|---|
| 3,025,464 | 3/1962 | Bond | 73/194 E |
| 3,160,745 | 12/1964 | Foster | 73/61.4 |
| 3,242,729 | 3/1966 | Keller | 73/194 E |
| 3,374,672 | 3/1968 | Horne | 73/194 E |
| 3,820,392 | 6/1974 | Beck et al. | 73/194 E |
| 3,936,729 | 2/1976 | Winslow | 73/194 E |

Primary Examiner—Anthony V. Ciarlante
Attorney, Agent, or Firm—Morgan, Finnegan, Pine, Foley & Lee

[57] ABSTRACT

An electric device is disclosed which is intended to detect and to signal the beginning of the settling of the solid phase of a solid-in-liquid suspension of a particulate, said suspension flowing in a duct for long-distance conveying of said particulate. The device essentially comprises a set of polarizing electrodes and a set of detecting electrodes. The signals delivered by the device are properly displayed after processing and characteristic patterns of the suspension flow can be viewed on an oscilloscope or, if desired, graphically recorded.

4 Claims, 4 Drawing Figures

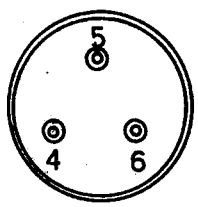
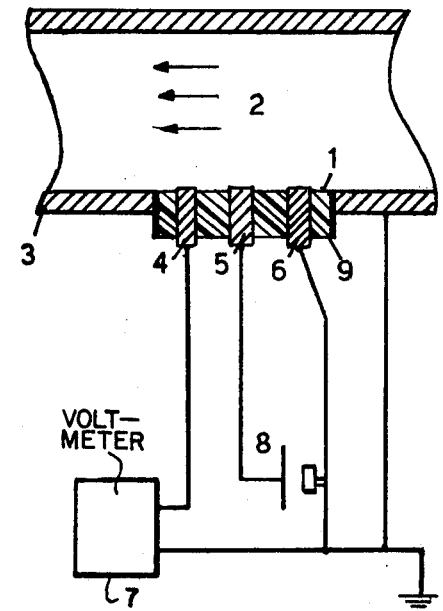
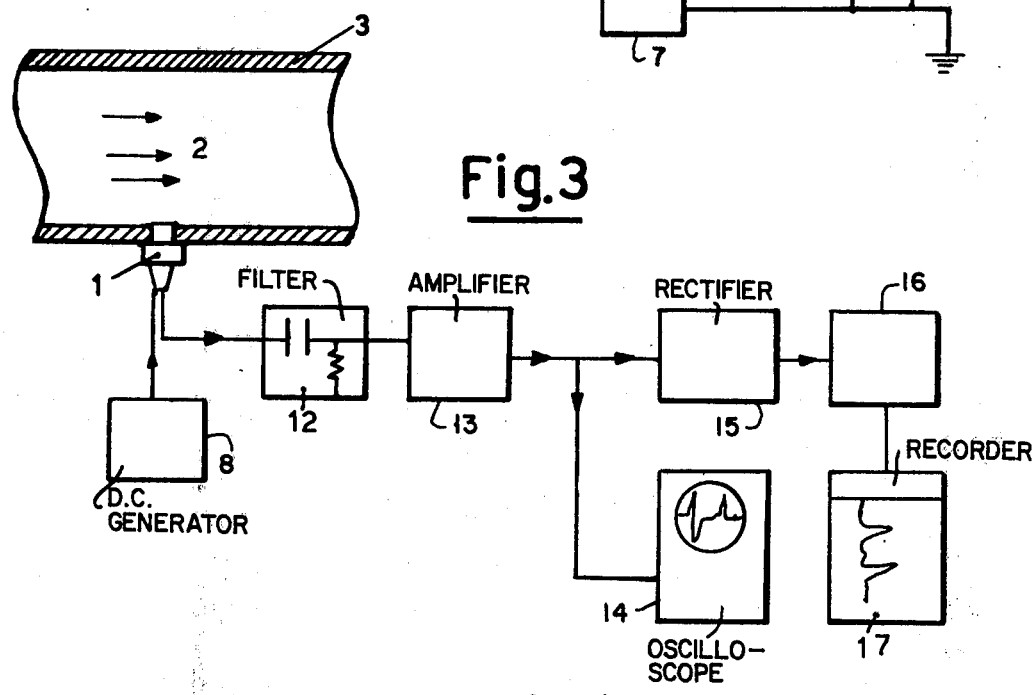
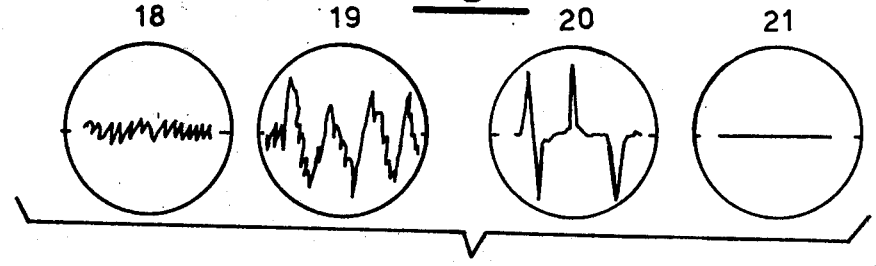

DEVICE FOR DETECTING THE INITIAL SETTLING OF THE SOLID PHASE IN SOLID-LIQUID SUSPENSIONS

This invention relates to a device for detecting the initial settling of the solid phase in solid-liquid suspensions.

When studying the methods of conveyance of materials suspended in the water flowing in a duct, it is particularly important to detect the so-called "critical speed" which is the speed in correspondence with which the conveyed material shows a tendency to settle.

The detection of the critical speed, or more generally the motion situation and the phenomena which forerun and accompany it when the rate of flow of the conveying fluid becomes gradually reduced, involves particular difficulties due to the properties of the liquid-suspension system, such as the abrasive properties and the opacity to light. The latter property prevents the adoption of current optical methods, such as the direct vision method or the use of interferometric methods. The presence of particles in suspension, in addition, disturbes the probes for detecting the local velocity in Pitot tubes and like apparatus. The methods which employ hot film heat probes are not readily adapted to such a type of investigation due to the abrasion of the sensitive element. Positive results have been obtained with devices for detecting local velocities of the electromagnetic type but these latter devices, in addition to being responsive also to the magnetic properties of the duct and the conveyed solid particulate, require apparatus which are particularly intricate and expensive.

An object of the present invention is to provide a device which is adapted to detect particular properties of a flowing mass when the suspension is near the critical speed.

The detection in question is achieved by an electric probe which is characterized by the presence of two sets of electrodes, the first of which has the function of a polarizing group and the second has the function of a detecting unit.

In order that the operation of such a probe may be better understood it is fitting to remember (see for example I. Kazanskij: Friction Losses and Macroturbulent Intensity in Two-Phase Pipe Flows, World Dredging and Marine Construction, September 1973, page 23), that, when passing from such speeds as to provide a correct conveyance of the suspension at lower speeds near to the critical speed, there is observed an increase of the intensity of the macroturbulence and a decrease of the frequency of the whirls. In an adequately small interval centered on the critical speed the phenomenon of mobile dunes is observed, which is due to the formation of unstable deposits of particulate on the bottom of the conduit and their instability can be expressed in terms of a low-frequency pulsatory motion.

At lower speeds outside of the interval aforementioned, the formation of stationary deposits is experienced.

The study of the conditions of "critical speed" can thus be effected by observing the flow of a suspension in the vicinity of the bottom generating line of the conduit. The probe according to the invention permits detecting such a flow in a simple, reliable, easy to install way without suffering from any restriction as to the size of the conduit required. The probe, more particularly, is capable of detecting fluids having, generally speaking, a certain degree of ionic dissociation, for example, suspensions of solid particles in natural waters. The degree of dissociation is assumed to be constant in the following discussion for the sake of simplification.

The probe according to the invention will now be illustrated by practical examples which do not limit either the structure or the field of application thereof.

FIG. 1 is a diagrammatical showing of the probe according to the invention as a whole.

FIG. 2 is a top plan view of the probe.

FIG. 3 is a diagrammatical showing of a possible assembly of the probe and the detection and measuring apparatus associated therewith.

FIG. 4 is a set of signal plots relating to different situations in the fluid suspension.

In FIG. 1, the probe 1 comprises the electrodes 4, 5 and 6, insulated from each other by the dielectric 9. The probe 1 includes a polarization group consisting of the electrodes 5 and 6 and a detection group comprising the electrode 4. Between the electrodes 5 and 6, a difference of electric potential is maintained by means of an appropriate D.C. generator 8 so as to induce an overall motion of the ions which are present in the suspension 2 flowing through the duct 3, the direction of flow being indicated by arrows.

This difference of electric potential could also be generated, as it is apparent, by an electrochemical effect using appropriate materials for the electrodes 5 and 6.

In the area in which the electrodes 4, 5 and 6 are located, motion is induced in the suspension 2 as a result of distribution and concentration of the electric charges which is a function of the intensity of the electric field and of the speed of the suspension. The second detection and measuring unit comprises the electrode 4 and is so positioned as to become involved in the motion of the ions which is originated by the first group (electrodes 5 and 6). The electrode 4 becomes electrically charged to take a potential which is related to the equilibrium between the taken up and delivered charges.

It thus becomes possible to obtain an electric signal between the measuring electrode 4 and a reference electrode which is usually the ground electrode 6. In view of the foregoing, with respect to the influence of the motion of the suspension on the situation of the motion, the distribution and the concentration of the charges in the inter-electrode area, there is obtained at the measuring electrode 4 a signal which is varied as the speed of flow of the suspension is varied.

As a rule, the signal has two components, an DC component and an AC component. The former relates to the overall motion of the suspension as a whole, considering constant, for convenience, the degree of dissociation. The second component essentially relates to the macroturbulence phenomena and thus its absence makes the settling of a layer of material in the electrode area conspicuous. The AC component can be detected by simple instruments of the V-meter type 7, and then it can properly be detected and processed.

It is thus apparent that the two units, the polarization unit and measuring unit, can each comprise a single electrode. In this case, the functions of the two units are combined in the sense that the two electrodes display both a polarizing and a detecting function.

The arrangement of the electrodes of the two units have an axial symmetry (concentrical cylindrical electrodes) in the case in which no sensitivity is required to the direction of the motion of the suspension, whereas it will have not such a symmetry in the opposite case.

FIG. 3 shows a possible use of the system proposed herein. The probe 1 referred to above is inserted in the bottom portion of the duct 3 through which a suspension, such as coal particles, lime particles and the like flows suspended in water, for conveyance over a long distance as a typical situation. The electrodes, as it is apparent, are made so as not to protrude into the interior of the duct. The signal delivered by the probe 1 is passed onto the high-pass filter 12 which has a cutoff frequency in the neighborhood of 0.1 Hertz. This provision eliminates the DC component of the signal. The signal is then amplified by the amplifier 13 and can be displayed, as a function of time, by an oscilloscope 14. The signal which has been amplified is further processed to obtain a more convenient display by a plotter 17. To this purpose, the A.C. signal is rectified at 15 by a circuit of the DC Restorer type and then passed onto a circuit 16 which delivers the mean value of the signal with a time constant of a few seconds, in order that detrimental oscillations are not be impressed on the writing point of the recorder 17.

Lastly, it is apparent that the signal can be processed by squaring procedures in order to obtain the RMS value which is significant in order to define the intensity of the turbulence or to apply methods of harmonic analysis or of correlation of the signal.

FIG. 4, diagrammatically shows trends of signals relative to typical conditions of flow. The numeral 18 shows a signal relating to a rapid motion of the suspension. The plot 19 is indicative of a signal trend relating to a slower motion, but still above the critical speed.

The plot 20 is a signal trend showing the "dunes" phenomenon.

The plot 21 shows a signal relating to the settling of the particulate in the suspension.

Possible application of the device according to the invention, in addition to those mentioned above, includes reservoirs in which it is required to check stirring in order to maintain a suspension homogeneous and free from settling. It is also apparent that the device according to the invention, when properly modified in the electric apparatus relative to the detection electrodes can be used for measuring the motion or motionless condition of fluids in general.

We claim:

1. A device for detecting the degree of settling of the solid phase of a solid-liquid suspension in a long-distance conveying duct comprising:
   a set of polarizing electrodes mounted to the duct and having a difference in potential maintained between said electrodes in order to induce an overall motion of the ions present in the suspension,
   at least one detecting and measuring electrode mounted to the duct in a predetermined position relative to one of said polarization electrodes to receive a signal due to the modification of the ionic distribution which varies as the speed and flow of the suspension varies,
   means to detect AC components of said signal,
   means to process said AC components, and,
   means using said processed components to indicate the degree of settling.

2. A device according to claim 1 wherein:
   the set of polarizing electrodes comprises at least two electrodes one of which has the function of ground reference.

3. A device according to claim 1 wherein:
   the measuring and detecting electrode comprises means for detecting a signal formed by the DC component of the suspension indicative of the motion of the suspension through the duct and by the AC component which is indicative of the degree of settling and is particularly due to the mobile dune phenomenon.

4. A device according to claim 1 wherein:
   the polarizing and measuring and detecting electrodes comprise a probe capable of mounting directly on ducts and substantially flush with the internal walls thereof.

* * * * *